United States Patent

Baker et al.

[11] 4,048,188
[45] Sept. 13, 1977

[54] 1-CARBONAMIDO IMIDAZOLES

[75] Inventors: Maurice W. Baker; John C. Kerry; Kenneth J. Nichol; John R. Marshall; David M. Weighton; Antonin Kozlik, all of Nottingham, England

[73] Assignee: The Boots Company Limited, Nottingham, England

[21] Appl. No.: 543,285

[22] Filed: Jan. 22, 1975

Related U.S. Application Data

[62] Division of Ser. No. 311,009, Nov. 30, 1972, Pat. No. 3,868,458.

[30] Foreign Application Priority Data

Dec. 7, 1971   United Kingdom ............... 56781/71
July 26, 1972  United Kingdom ................ 3498/72

[51] Int. Cl.$^2$ ........................................... C07D 233/56
[52] U.S. Cl. ..................................... 548/341; 544/139
[58] Field of Search ................. 260/247.1, 247.2, 243, 260/309, 293.6

[56] References Cited

U.S. PATENT DOCUMENTS 3,374,241   3/1968   Giberson .............................. 260/309

Primary Examiner—Henry R. Jiles
Assistant Examiner—R. W. Ramsuer
Attorney, Agent, or Firm—Lawrence Rosen; E. Janet Berry

[57] ABSTRACT

New imidazole compounds, pesticidal compositions and methods of using them, and their preparation are described. The compounds have the formula

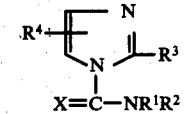

in which X is oxygen or sulphur, $R^3$ is hydrogen, alkyl or alkenyl, $R^4$ is alkyl or cycloalkyl, and $R^1$ and $R^2$ are each lower alkyl or alkenyl, $R^1$ is lower alkyl and $R^2$ is alkoxyalkyl or haloalkyl, or $R^1$ and $R^2$ together with the nitrogen atom to which they are attached, from a heterocyclic ring. Novel compounds are of particular value against insects e.g. aphids, and against other pests, e.g. acarids.

4 Claims, No Drawings

1-CARBONAMIDO IMIDAZOLES

The present application is a divisional application of Ser. No. 311,009, filed Nov. 30, 1972, now U.S. Pat. No. 3,868,458.

This invention relates to new chemical compounds, insecticidal compositions containing the new compounds as active ingredient, and the use of the new compounds to control insects.

According to one feature of the invention there is provided a new group of compounds which may be represented by the general formula

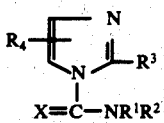

(I)

in which X is oxygen or sulphur, $R^3$ is hydrogen, alkyl or alkenyl, $R^4$ is alkyl or cycloalkyl, and (a) $R^1$ and $R^2$ are each lower alkyl or lower alkenyl (b) $R^1$ is lower alkyl and $R^2$ is alkoxyalkyl or lower haloalkyl, or (c) $R^1$ and $R^2$, together with the nitrogen atom to which they are attached, form a heterocyclic ring, optionally containing 1 to 4 lower alkyl substituents attached to carbon atoms of the heterocyclic ring, selected from morpholino, thiamorpholino, 1-pyrrolidinyl and 1-piperidino.

A preferred group of compounds is one in which (a) $R^1$ is methyl and $R^2$ is lower alkyl or lower alkenyl, (b) $R^1$ and $R^2$ are both ethyl, propyl or allyl, or (c) $R^1$ and $R^2$, together with the nitrogen atom to which they are attached, form a heterocyclic ring, optionally containing 1 to 4 lower alkyl substituents attached to carbon atoms of the heterocyclic ring, selected from morpholino, thiamorpholino, 1-pyrrolidinyl and 1-piperidino. Preferred compounds are often those in which X in the above general formula is oxygen.

The radical $R^3$ may have a straight or branched chain and may contain, for example, up to 10 carbon atoms. Thus $R^3$ may be, for example, hydrogen, methyl, ethyl, propyl, isopropyl, n-butyl, isobutyl, sec.butyl, tert.butyl, n-pentyl, isopentyl, n-hexyl, n-heptyl, 1,1-diethylpropyl, n-octyl, 2-ethylhexyl, n-nonyl, n-decyl, allyl, 1-propenyl 3-butenyl. Most suitably $R^3$ is hydrogen, or lower alkyl such as propyl, isopropyl, n-butyl, sec.butyl, isobutyl, tert.butyl and especially methyl and ethyl.

The radical $R^4$ is alkyl or cycloalkyl and may contain, for example, up to 10 carbon atoms. Thus when $R^4$ is alkyl it may have a straight or branched chain, may be a primary, secondary or tertiary radical, for example, methyl, ethyl, propyl, isopropyl, n-butyl, isobutyl, sec.-butyl, tert.butyl, 1-methylbutyl, 1-ethylpropyl, n-pentyl, isopentyl, tert.pentyl, n-hexyl, 1,1,2-trimethylpropyl, n-heptyl, 1,1-diethylpropyl, 2,3,3-trimethylbut-2-yl, n-octyl, 2-ethylhexyl, n-nonyl or n-decyl. Preferred values of $R^4$ when it is an alkyl group, are tert.butyl, sec.butyl, propyl, 1-ethyl propyl, isopropyl and tert.-pentyl. When $R^4$ is cycloalkyl it may contain, for example, up to 8, and more preferably from 3 – 7, carbon atoms in the cyclo ring. The cycloalkyl group may optionally contain one or more substituents on the ring, for example, one or more lower alkyl (especially methyl) substituents. A lower alkyl substituent is preferably in the 1-position, that is, it is attached to the cycloalkyl carbon atom joined to the imidazole ring. A further preferred group contains a lower alkyl (especially methyl) substituted in the 1-position and in addition one or more lower alkyl (especially methyl) substituents in other positions on the ring. When there is more than one substituent on the cycloalkyl group they may be the same or different. Thus, for example, typical values for $R^4$ are cyclopropyl, 1-methylcyclopropyl, 2-methylcyclopropyl, 2,2-dimethylcyclopropyl, cyclobutyl, 1-methylcyclobutyl, cyclopentyl, 1-methylcyclopentyl, 1-ethylcyclopentyl, 2, 3 or 4 methylcyclopentyl, cyclohexyl, 1-methylcyclohexyl, 1-methylcyclohexyl containing 1, 2 or 3 further methyl substituents such as for example 1,3-dimethylcyclohexyl, 1,4-dimethylcyclohexyl, 1,3,3-trimethylcyclohexyl; 1-ethylcyclohexyl, 2, 3 or 4 methylcyclohexyl, 2,4-dimethylcyclohexyl, 2, 3 or 4 ethylcyclohexyl, cycloheptyl or cyclooctyl. Preferably, when $R^4$ is cycloalkyl, it contains five or six carbon atoms in the cyclo ring and is cyclopentyl optionally containing one or more methyl substituents or cyclohexyl optionally containing one or more methyl substituents. Specific examples include cyclopentyl, 1-methylcyclopentyl, cyclohexyl, 1-methylcyclohexyl, 1,3-dimethylcyclohexyl 1,3,3-trimethylcyclohexyl.

When the group $NR^1R^2$ is an acyclic group both $R^1$ and $R^2$ may have a straight or branched chain and (a) $R^1$ and $R^2$ are the same or different and are lower alkyl or lower alkenyl; examples of lower alkenyl are methyl, ethyl, propyl, isopropyl, or n-butyl, isobutyl, sec.butyl, tert. butyl, n-pentyl, isopentyl, n-hexyl or n-heptyl; lower alkenyl may contain for example 2 to 4 carbon atoms, especially allyl, (b) $R^1$ is lower alkyl and $R^2$ is alkoxyalkyl, containing for example from 3 to 6 carbon atoms such as ethoxyethyl, or lower haloalkyl containing for example from 1 to 6 carbon atoms and substituted by one or more halogen atoms preferably fluorine, chlorine or bromine. It is preferred that either (a) $R^1$ is methyl and $R^2$ is lower alkyl or (b) $R^1$ and $R^2$ are both ethyl or propyl. A specially preferred group of compounds is that in which $R^1$ is methyl and $R^2$ is lower alkyl, preferably containing 1–4 carbon atoms and especially methyl.

As hereinbefore mentioned, when the group $NR^1R^2$ is a heterocyclic group, it may contain 1–4 lower alkyl (especially methyl) substituents attached to carbon atoms of the heterocyclic ring. Such alkyl-substituted heterocyclic groups include, for example, 2,6-dimethylmorpholino, 4-methyl-1-piperidino, 2-methyl-1-piperidino, 2,6-dimethyl-1-piperidino and 2-ethyl-1-piperidino. When $NR^1R^2$ is heterocyclic it is preferably morpholino, 1-pyrrolidinyl or 1-piperidino.

We have found that the compounds of the present invention have pesticidal activity and, for example, can be used to combat insects. The compounds have activity against Diptera such as the larvae of the sheep blow fly, *Lucilia sericata* and species of Hemiptera. For example they are of use against California red scale, *Acridiella aurantii*, the Comstock mealybug, *Pseudococcus comstocki* and plant hoppers such as, for example, the green rice leafhopper, *Nephotettix cincticeps*. They are especially useful in controlling aphids such as *Aphis fabae, Megoura viciae, Myzus persicae, Phorodon humuli, Eriosoma langerum, Brevicoryne brassicae* and *Acrythosiphon pisum*. The compounds also have acaricidal activity against adults of the two-spotted mite, *Tetranychus urticae* and the citrus red mite, *Panonychus citri*.

According to a further feature of the present invention there are provided pesticidal, in particular insecticidal such as for example aphicidal, compositions which comprise as an active ingredient a compound of the present invention together with a diluent or carrier. The diluent or carrier may be a solid or a liquid, optionally in association with a surface-active agent, for example, a dispersing agent, emulsifying agent or wetting agent.

The compositions of the present invention may take any of the forms known in the art for the formulation of pesticidal or insecticidal compounds, for example solutions, aqueous dispersions, aqueous emulsions, dusting powders, dispersible powders, fumigants, emulsifiable concentrates and granules. Such compositions include not only compositions in a suitable form for application but also concentrated primary compositions which require dilution with a suitable quantity of water or other diluent before application. Dispersible powders and emulsifiable concentrates are typical examples of such primary compositions.

As dispersions, the compositions comprise essentially a compound of the invention dispersed in an aqueous medium. It is convenient to supply the consumer with a primary composition which may be diluted with water to form a dispersion having the desired concentration; the primary composition may be in any one of the following forms. It may be provided as a dispersible solution which comprises a compound of the invention dissolved in a water-miscible solvent with the addition of a dispersing agent. Alternatively it may be provided as a dispersible powder which comprises a compound of the invention and a dispersing agent. A further alternative comprises a compound of the invention in the form of a finely ground powder in association with a dispersing agent and intimately mixed with water to give a paste or cream. This paste or cream may if desired be added to an emulsion of oil in water to give a dispersion of active ingredient in an aqueous oil emulsion.

Emulsions comprise essentially a compound of the invention dissolved in a water-immiscible solvent which is formed into an emulsion with water in the presence of an emulsifying agent. An emulsion of the desired concentration may be formed from a primary composition of the following types. A concentrated stock emulsion may be supplied comprising a compound of the invention in combination with an emulsifying agent, water and a water-immiscible solvent. Alternatively there may be supplied an emulsifiable concentrate comprising a solution of a compound of the invention in a water-immiscible solvent containing an emulsifying agent.

A dusting powder comprises a compound of the invention intimately mixed and ground with a solid pulverulent diluent, for example kaolin.

A granular solid may comprise a compound of the invention associated with similar diluents to those which may be employed in dusting powders, but the mixture is granulated by known methods. Alternatively they may comprise the active ingredient absorbed on a pre-formed granular diluent for example fullers earth, attapulgite and limestone grit.

The concentration of the active ingredient in the primary compositions of the present invention may vary widely and may be, for example, 5-95% w/w of the composition. The concentration of the active ingredient in the compositions of the present invention for application to control pests, especially insects such as aphids, is generally within the range 0.001-10% w/w, especially 0.005-5% w/w.

According to a further feature of the present invention there is provided a method for combating pests, especially insects, which comprises applying a compound of the present invention to the locus of the pests, i.e. the pests or their habitat. A particular embodiment of this feature is a method for protecting plants from insects, and in particular aphids, which comprises applying a compound of the present invention to the locus of the plants, i.e. the plants or their habitat.

In combating pests the active compound can be applied on its own or preferably as one of the compositions described above. Direct treatment is often the preferred method, by for example, spraying, dusting or fumigation of plants infested with insects. Alternatively the active compound can be applied to the soil in which plants are grown as granules or as a root drench. In such instances the active compound is absorbed by the roots of the plant rod confers protection from the insects. A suitable application rate of the compound of the present invention is generally within the range 0.005-10 lb./acre, more usually 0.01-5 lb./acre. The compounds of the present invention may be used to protect a variety of plants from aphids, for example ornamental plants such as roses, and crop plants such as fruit trees, leguminous crops, potatoes, hops, sugar beet, cotton, maize, rice and tobacco.

A composition of the invention may comprise as active ingredient more than one compound of the general formula I and it may also comprise one or more additional pesticide or, for example, a fungicide or insecticide for example an organochlorine or organophosphorus insecticide.

The compounds of the present invention may be prepared by a process which comprises reacting an imidazole of the general formula

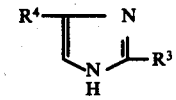

(II)

in which $R^3$ and $R^4$ are as hereinbefore defined with a carbamoyl halide or thiocarbamoyl halide of the general formula $Z-CXNR^1R^2$ (III) in which $R^1$, $R^2$ and X are as hereinbefore defined and Z is halogen, for example, chlorine or bromine preferably chlorine. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine, in order to absorb the hydrogen halide produced in the reaction. In preparing the compounds by this route the reactants are preferably reacted together at a temperature of from 0° to 120° C., for example from 50° to 95° C.

The carbamoyl halides or thiocarbamoyl halides of the general formula (III) may be prepared by reacting a secondary amine of the general formula $HNR^1R^2$ with a carbonyl halide or thiocarbonyl halide of the general formula $CXZ_2$ in which Z is preferably chlorine, in accordance with known methods.

The compounds of the present invention may also be prepared by a process which comprises reacting a carbamoyl halide or thiocarbamoyl halide of the general formula (IV)

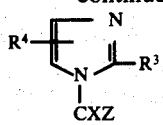

in which $R^3$, $R^4$ and Z are as hereinbefore defined, Z being halogen preferably chlorine, with a secondary amine of the general formula $HNR^1R^2$, $R^1$ and $R^2$ being defined hereinbefore. The reaction is suitably effected in the presence of an inert organic liquid as the reaction medium, which is preferably a solvent for the reactants, at a temperature from −5° to 50° C. Advantageously the reaction is effected in the presence of a suitable acid-binding agent, for example a tertiary amine such as triethylamine or pyridine.

The compounds of the general formula IV are preferably prepared in situ from the imidazoles of general formula II by reaction with a carbonyl halide or thiocarbonylhalide $CXZ_2$, in which Z is preferably chlorine, suitably in the presence of solvent and acid-binding agent; the secondary amine reactant then being added to the reaction product.

The compounds of the present invention may also be prepared by a process which comprises reacting a carbonylbisimidazole of thiocarbonylbisimidazole of the general formula

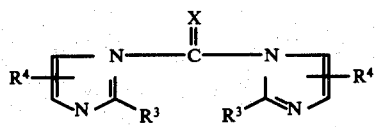

(V)

in which $R^3$, $R^4$ and X are as hereinbefore defined, with a secondary amine of the general formula $HNR^1R^2$, $R^1$ and $R^2$ being defined hereinbefore. The reaction is suitably effected in the presence of an inert organic liquid as the reaction medium, which is preferably a solvent for the reactants, at a temperature of, for example, from −5° to 50° C.

The compounds of the general formula V are preferably prepared in situ by reacting an imidazole of the general formula II with about 0.5 molecular proportions of a carbonyl halide or thiocarbonyl halide $CXZ_2$, in which Z is preferably chlorine; the secondary amine then being added to this reaction product. The reaction is preferably effected in the presence of a suitable acid-binding agent, for example a tertiary amine such as triethylamine or pyridine.

It will be appreciated that the reactions described above may give either or both of two isomeric products, depending on which nitrogen atom in the imidazole ring is substituted (the free hydrogen of the imidazole molecule of formula II can be associated with either of the ring nitrogen atoms). Since it may not be possible to distinguish between these isomers, the products of the present invention may be conveniently designated as 1-(N,N-disubstituted-carbamoyl or thiocarbamoyl)-2-$R^3$-4(5)-$R^4$-imidazoles. This designation corresponds to formula I which encompasses both of the isomeric forms. The current state of our knowledge indicates that the solid products of the reactions described above, after purifications by conventional techniques such as crystallization, are obtained in many instances as substantially pure 4-substituted compounds. The current state of our knowledge also indicates that the liquid products of the reactions described above, after isolation by conventional techniques such as distillation in vacuo, are obtained in many instances substantially or predominantly in the 4-substituted isomeric form. It will be appreciated that such isomers may be designated as 1-(N,N-disubstituted-carbamoyl or thiocarbamoyl)-2-$R^3$-4-$R^4$-imidazoles.

The following examples illustrate the invention.

EXAMPLE 1

To a stirred mixture of 173 g. 4-tert.butylimidazole, 205 ml. triethylamine and 300 ml. dry tetrahydrofuran was gradually added 167 g. dimethylcarbamoyl chloride. An exothermic reaction ensued, and the rate of addition of dimethylcarbamoyl chloride was adjusted so as to maintain a gentle boiling of the reaction mixture under reflux. When addition of the dimethylcarbamoyl chloride was complete, the reaction mixture was boiled under reflux with stirring for 1 hour, and then cooled to room temperature. The reaction mixture was diluted with 200 ml. water and then extracted with diethyl ether (2 × 200 ml.). The ethereal extracts were combined, dried over anhydrous sodium sulphate and evaporated. The resulting residue was crystallized from light petroleum (b.p. 100°–120° C.) and recrystallized from di-isopropyl ether to give 1-dimethylcarbamoyl-4(5)-tert.butylimidazole, m.p. 85°–86° C. The current state of our knowledge indication that this compound is 1-dimethylcarbamoyl-4-tert.butylimidazole.

EXAMPLE 2

In an analogous manner to that described in Example 1, there was prepared 1-dimethylcarbamoyl-4(5)-methylimidazole, m.p. 58°–60° C. (crystallized from light petroleum b.p. 100°–120° C. and recrystallized from methylcyclohexane). The current state of our knowledge indicates that this compound is 1-dimethylcarbamoyl-4-methylimidazole.

EXAMPLE 3

A solution of 2.46 g. 4-tert.butylimidazole, 1.0 g. triethylamine and 2.42 g. N-ethyl-N-methylcarbamoyl chloride in 20 ml. dry tetrahydrofuran was boiled under reflux for 6.5 hours. The reaction mixture was cooled to room temperature and filtered to remove triethylamine hydrochloride. Solvent was removed from the resulting filtrate by evaporation under reduced pressure and the residue was distilled under reduced pressure to give 1-(N-methyl-N-ethylcarbamoyl)-4(5)-tert.butylimidazole, b.p. 99°–101° C./0.1 mm.

In an analogous manner to that described above, there were prepared the following compounds.

1-dimethylthiocarbamoyl-4(5)-tert.butylimidazole, b.p. 140°–141° C./1.0 mm.

1-(N-methyl-N-propylcarbamoyl)-4(5)-tert.butylimidazole, b.p. 120°–122° C./0.5 mm.

1-(N-methyl-N-heptylcarbamoyl)-4(5)-tert.butylimidazole, b.p. 154°–156° C./0.7 mm.

1-diallylcarbamoyl-4(5)-tert.butylimidazole, b.p. 120°–121° C/0.2 mm.

1-(N-methyl-N-allylcarbamoyl)-4(5)-tert. butylimidazole, b.p. 126°–128° C./1.0 mm.

1-dimethylcarbamoyl-2-ethyl-4(5)-methylimidazole, b.p. 85° C./0.15 mm.

1-dimethylcarbamoyl-4(5)-n-pentylimidazole, b.p. 120° C./0.9 mm.

1-dimethylcarbamoyl-4(5)-isobutylimidazole, b.p. 104° C/0.13 mm.
1-dimethylcarbamoyl-4(5)-isopropylimidazole, b.p. 98° C./0.13 mm.
1-dipropylcarbamoyl-4(5)-isobutylimidazole, b.p. 104°-106° C./0.05 mm.
1-dipropylcarbamoyl-4(5)-isopropylimidazole, b.p. 108° C./0.12 mm.
1-dimethylthiocarbamoyl-4(5)-isopropylimidazole, b.p. 107°-114° C./0.03 -0.05 mm.
1-dimethylcarbamoyl-4(5)-(1-ethylpropyl)imidazole, b.p. 112° C./0.15 mm.
1-dipropylcarbamoyl-4(5)-(1-ethylpropyl)imidazole, b.p. 100°-106° C./0.25 -0.03 mm.
1-dimethylcarbamoyl-2-methyl-4(5)-methylimidazole, b.p. 80°-84° C./0.7-0.1 mm.
1-dimethylcarbamoyl-4(5)-isopropylimidazole, b.p. 98° C./0.13 mm.
1-dimethylthiocarbamoyl-2-ethyl-4(5)-methylimidazole, b.p. 128°-130° C./0.3 mm.
1-dimethylcarbamoyl-4(5)-sec.butylimidazole, b.p. 95° C./0.04 mm.
1-(2,6-dimethylmorpholinocarbonyl)-4(5)-tert.butylimidazole, b.p. 154° C./1.0 mm.

The current state of our knowledge indicates that the 4(5) alkyl groups of the imidazoles listed above are predominantly or substantially in the 4-position.

EXAMPLE 4

A mixture of 5.52 g. 4-tert.-butylimidazole, 6.1 g. triethylamine, 8.95 g. morpholinocarbonyl chloride and 30 ml. dry tetrahydrofuran was boiled under reflux for 5 hours. The reaction mixture was diluted with 100 ml. methylene dichloride, cooled to room temperature, and washed with water to remove triethylamine hydrochloride. The resulting organic solution was dried over anhydrous magnesium sulphate and then evaporated to dryness. The resulting solid residue was recrystallized from ethanol to give 1-morpholinocarbonyl-4(5)-tert.butylimidazole, m.p. 129°-130° C. The current state of our knowledge indicates that this compound is 1-morpholinocarbonyl-4-tert.butylimidazole.

EXAMPLE 5

A mixture of 5.0 g. 4-tert-butylimidazole, 4.4 g. triethylamine, 5.9 g. 1-piperidinocabonyl chloride and 30 ml. dry tetrahydrofuran was boiled under reflux for 5.5 hours. The reaction mixture was cooled, filtered to remove triethylamine hydrochloride, and evaporated to dryness. The resulting solid residue was recrystallized from petroleum (b.p. 62°-68° C.) to give 1-piperidinocarbonyl-4(5)-tert.butylimidazole, m.p. 104°-105° C.

The following compound was prepared in an analogous manner.

1-(1-pyrrolidinylcarbonyl)-4(5)-tert.butylimidazole, m.p. 124°-126° C.

The current state of our knowledge indicates that the 4-tert.butyl group in the above compounds is in the 4-position.

EXAMPLE 6

In an analogous manner to that described in Example 3, the following compounds were prepared.

1-(N-methyl-N-2-ethoxyethylcarbamoyl)-4(5)-tert.butylimidazole, b.p. 137°-138° C./0.4 mm.
1-dimethylcarbamoyl-4(5)-propylimidazole, b.p. 108° C./0.27 mm.
1-dimethylcarbamoyl-4(5)-butylimidazole, b.p. 109° C./0.1 mm.
1-morpholinocarbonyl-4(5)-sec.butylimidazole, b.p. 119°-126° C./0.05 mm.
1-morpholinocarbonyl-4(5)-isobutylimidazole, b.p. 136°-138° C./0.15 mm.
1-morpholinocarbonyl-4(5)-butylimidazole, b.p. 126°-127° C./0.02 mm.
1-(N-methyl-N-butylcarbamoyl)-4(5)-tert.butylimidazole, b.p. 152°-154° C./2.0 mm.
1-(N-methyl-N-pentylcarbamoyl)-4(5)-tert.butylimidazole, b.p. 160°-162° C/2.0 mm.
1-(N-methyl-N-hexylcarbamoyl)-4(5)-tert.butylimidazole, b.p. 170°-172° C./2.0 mm.
1-piperidinocarbonyl-4(5)-isopropylimidazole, b.p. 170°-175° C./3.0 mm.
1-piperidinocarbonyl-4(5)-sec.butylimidazole, b.p. 190° c./8 mm.
1-pyrrolidinylcarbonyl-4(5)-sec.butylimidazole, b.p. 208° C./22 mm.
1-diethylcarbamoyl-4(5)-sec.butylimidazole, b.p. 165° C./6 mm.
1-(N-methyl-N-ethylcarbamoyl)-4(5)-isopropylimidazole, 160°-164° C./9.0 mm.
1-morpholinocarbonyl-4(5)-isopropylimidazole, b.p. 180°-185° C./5.0 mm.
1-dimethylthiocarbamoyl-4(5)-1-methylbutyl)imidazole b.p. 180°-185° C./5.5 mm.
1-dimethylthiocarbamoyl-4(5)-(1-methylbutyl)imidazole b.p. 165°-170° C./4 mm.
1-(N-methyl-N-ethylcarbamoyl)-4(5)-sec.-butylimidazole, b.p. 178° C./28 mm.
1-(N-methyl-N-ethylthiocarbamoyl)-4(5)-sec.-butylimidazole b.p. 182° C./7 mm.
1-dimethylcarbamoyl-4(5)-(1,2-dimethylbutyl)imidazole, b.p. 125° C./0.15 mm.
1-dimethylcarbamoyl-4(5)-(1-methylheptyl) imidazole, b.p. 125° C./0.02 mm.
1-dimethylcarbamoyl-4(5)-(1-methylpentyl)imidazole, b.p. 128° C./0.5 mm.
1-morpholinocarbonyl-4(5)-isopropylimidazole, b.p. 124° C./0.14 mm.
1-dimethylthiocarbamoyl-4(5)-tert.pentylimidazole, b.p. 180°-185° C./6.0 mm.

The current state of our knowledge indicates that the above compounds were obtained predominantly or substantially as the 4-substituted compounds.

EXAMPLE 7

To a stirred solution of 14 g. 4-tert.pentylimidazole in 100 ml dry tetrahydrofuran and 28 ml. triethylamine was gradually added 13 g. dimethylcarbamoyl chloride. When addition of the carbamoyl chloride was complete the reaction mixture was boiled under reflux with stirring for one hour, then cooled to room temperature and poured on to 500 g. water and crushed ice. After extraction with ether, the ether layer was separated, washed with water and dried over anhydrous magnesium sulphate. The ether was evaporated and a residue remained which was crystallized from petroleum ether (b.p. 60°-80° C.) to give the product, 1-dimethylcarbamoyl-4(5)tert.pentylimidazole, m.p. 60-61° C. The current state of our knowledge indicates that this compound is 1-dimethylcarbamoyl-4-tert.pentylimidazole.

The 4-tert.pentylimidazole used in the above reaction was prepared in the following way:

A solution of 121.5 g. bromine in 150 ml. chloroform was added dropwise with stirring to a soluton of 87 g.

3,3-dimethylpentan-2-one in 360 ml methanol. The reaction was initiated by the addition of a few drops of bromine solution at 15° C., then cooled to 0° C. and addition of bromine continued whilst the temperature was maintained at 0°-5° C. After completion of the bromine addition the reaction mixture was stirred at 0°-5° C. for 10 minutes, then poured on to a mixture of crushed ice and water. The water layer was extracted with methylene dichloride and the extract added to the organic portion. The combined liquors were washed with water, saturated solution of sodium bicarbonate and then dried over calcium chloride. After evaporating the solvent under reduced pressure, 1-bromo-3,3-dimethylpentan-2-one distilled over, b.p. 84° C./9 mm.

A mixture of 111.5 g. 1-bromo-3,3-dimethylpentan-2-one and 300 ml. formamide was heated with stirring. A weak stream of ammonia was passed through the reaction mixture over a period of one hour, the temperature being maintained at from 140°-160° C. The stream of ammonia was then stopped and the reaction mixture maintained at a temperature of 160° C. for 2 hours. Excess of formamide was evaporated under reduced pressure, the residue diluted with a little warm water and basified with potassium carbonate. The imidazole was separated with ether, the ethereal extract being washed with water and dried over anhydrous sodium sulphate.

After evaporating the solvent under reduced pressure, the residue was distilled to give the product, 4-tert.pentylimidazole, b.p. 114°-116° C./0.2 mm. On standing this liquid solidified and the solid crystallized from petroleum ether (b.p. 60°-80° C.) to give a pure product having a melting point of 95°-96° C.

In an analogous way to that described above, the following compounds were prepared.

1-dimethylcarbamoyl-4(5)neopentylimidazole, m.p. 63°-66° C.
1-dimethylcarbamoyl-4(5)-(2,3,3 -trimethyl-but-2'-yl)imidazole, m.p. 70°-71° C.
1-morpholinocarbonyl-4(5)-tert.pentylimidazole, m.p. 98°-99° C.
1-pyrrolidinylcarbonyl-4(5)-tert.pentylimidazole, m.p. 109°-110° C.
1-dimethylcarbamoyl-4(5)-(1,1,2-trimethylpropyl-)imidazole, m.p. 85°-86° C.
1-(N-ethyl-N-methylcarbamoyl)-4(5)-tert.pentylimidazole, m.p. 38°-40° C.
1-morpholinocarbonyl-4(5)-(2,3,3-trimethylbut-2'-yl)imidazole, m.p. 122°-123° C.
1-(4-methylpiperidinocarbonyl)-4(5)-tert-.butylimidazole, m.p. 87° C.
1-(N-methyl-N-isopropylcarbamoyl)-4(5)-tert-.butylimidazole, m.p. 72°-73° C.
1-(N-methyl-N-2-chloroethylcarbamoyl)-4(5)-tert-.butylimidazole m.p. 84°-85° C.
1-pyrrolidinylcarbonyl-4(5)-isopropylimidazole, m.p. 70°-71° C.

The current state of our knowledge indicates that the above imidazoles were obtained predominantly or substantially as the 4-substituted compounds.

In the course of preparing the above compounds the following novel intermediates were made.

4-(2,3,3-trimethyl-but-2yl)imidazole, m.p. 149°-150° C.
4-(1,1,2-trimethylpropyl)imidazole, b.p. 110°-114° C./0.1 mm.
4-neopentylimidazole, b.p. 106°-114° C./0.15-0.19 mm.

EXAMPLE 8

To a stirred solution of 1.25 g. 2-methyl-4-tert-.butylimidazole in 10 ml. tetrahydrofuran and 2 ml. triethylamine was added 1.2 g. dimethylcarbamoyl chloride. The resulting mixture was boiled under reflux with stirring for 3½ hours and then cooled to room temperature. The reaction mixture was diluted with 100 ml. methylene chloride, washed with water, and the methylene chloride solution dried over magnesium sulphate. After evaporating the solvent the residue was distilled under reduced pressure to give 1-dimethylcarbamoyl-2-methyl-4(5)-tert.butylimidazole, b.p. 126°-127° C./1 mm. This liquid solidified on standing and when recrystallized from petroleum ether (b.p. 60°-80° C.) gave the pure product, m.p 80°-81° C. The current state of our knowledge indicates that this compound is 1-dimethylcarbamoyl-2-methyl-4-tert-.butylimidazole.

The imidazole used in the above reaction was prepared in the following way.

85 g. Bromopinacolone was added to a solution of 72 g. potassium acetate in 700 ml. methanol and the resulting mixture was refluxed on a steam bath for two hours. It was then cooled, filtered and the filtrate added with stirring to a solution of 190 g. cupric acetate monohydrate in 800 ml. water and 1000 ml. 25 percent ammonia. A solution of 26 g. acetaldehyde in 200 ml. water was then added to the mixture which was heated on a steam bath for 5 hours with constant stirring.

After cooling the cuprous salt of the imidazole was collected, washed with water and suspended in 500 ml. of 4N acetic acid. While stirring, a solution of 78 g. potassium ferricyanide in 240 ml. water was added and the precipitated copper complex removed and washed well with water. The combined supernatant liquors were basified to pH 9-10 with 5N sodium hydroxide and extracted several times with ether. The etheral extracts were combined, washed with water and dried over anhydrous sodium sulphate. After evaporation of the solvent under reduced pressure the residue distilled to give the imidazole product, b.p. 112°-114° C./0.05 mm. This solidified on standing and was recrystallized from a mixture of petroleum ether (60°-80° C.) containing a few drops of ethanol to give 2-methyl-4-tert-.butylimidazole, m.p. 155°-156° C.

In an analogous way to that described above, the following compounds were prepared.

1-dimethylcarbamoyl-2-ethyl-4(5)-tert-.butylimidazole, b.p. 108°-109° C./0.7 mm.
1-morpholinocarbonyl-2-ethyl-4(5)-tert-.butylimidazole, b.p. 124°-126° C./0.15 mm.
1-dimethylcarbamoyl-2-isopropyl-4(5)-tert-.butylimidazole, b.p. 86° C./0.1 mm., m.p. 57°-58° C.
1-dimethylcarbamoyl-2-butyl-4(5)-tert-.butylimidazole, b.p. 108°-110° C./0.2 mm.
1-morpholinocarbonyl-2-butyl-4(5)-tert-.butylimidazole b.p. 138°-141° C./0.4 mm.
1-dimethylcarbamoyl-2-isobutyl-4(5)-tert-.butylimidazole, b.p. 106°-108° C./0.25 mm.
1-dimethylcarbamoyl-2-(1-methylbutyl)-4(5)-tert-.butylimidazole, b.p. 98°-100° C./0.15 mm.
1-dimethylcarbamoyl-2-sec.butyl-4(5)-tert-.butylimidazole, b.p. 102°-104° C./0.25 mm.
1-dimethylcarbamoyl-2-(2,6-dimethylhept-5-enyl)-4(5)-tert. butylimidazole, b.p. 154°-156° C./0.4 mm.

1-dimethylcarbamoyl-2-(1-ethylpropyl)-4(5)-tert-butylimidazole, b.p. 97°–98° C./0.15 mm.

The current state of our knowledge indicates that the above imidazoles were obtained predominantly or substantially as the 4-substituted compounds.

In the course of preparing the above compounds the following novel intermediates were made.

2-ethyl-4-tert.butylimidazole, m.p. 154°–155° C.
2-isopropyl-4-tert.butylimidazole, m.p. 182° C.
2-butyl-4-tert.butylimidazole, m.p. 70°–72° C.
2-isobutyl-4-tert.butylimidazole, m.p. 128°–129° C.
2(1-methylbutyl)-4-tert.butylimidazole, m.p. 108°–109° C.
2-sec.butyl-4-tert.butylimidazole, m.p. 136° C.
2-(1-ethylpropyl)-4-tert.butylimidazole, m.p. 145°–146° C.

EXAMPLE 9

This example describes an alternative method of preparing 1-dimethylcarbamoyl-4(5)-tert.butylimidazole.

A solution of 6.2 g. tert.butylimidazole (0.05 mole) and 4 g. pyridine in 15 ml. dry tetrahydrofuran was added dropwise to a stirred solution of 2.5 g. phosgene (0.025 mole) in 25 ml. dry tetrahydrofuran maintained at a temperature of 0° to 5° C. The mixture was stirred for an hour and filtered. To the filtrate was gradually added a cold solution of 1.37 g. anhydrous dimethylamine (0.03 mole) in 15 ml. dry tetrahydrofuran at 0° C. The mixture was stirred for 2 hours at 0° to 5° C., filtered and the solvent evaporated. The residue distilled under reduced pressure to give a fraction having b.p. 102° C./0.5 mm. which solidified on cooling. After crystallization from petroleum ether (60°–80° C.) the pure product, 1-dimethylcarbamoyl-4(5)-tert.butylimidazole m.p. 85°–86° C., was isolated. The current state of our knowledge indicates that this compound is 1-dimethylcarbamoyl-4-tert.butylimidazole.

EXAMPLE 10

This example describes an alternative method of preparing 1-dimethylcarbamoyl-4(5)-tert.butylimidazole.

A solution of 6.2 g. tert.butylimidazole (0.05 mole) and 16 g. pyridine in 15 ml. dry tetrahydrofuran was added dropwise to a stirred solution of 5 g. phosgene (0.05 mole) in 50 ml. dry tetrahydrofuran at a temperature of 0° to 5° C. The mixture was stirred for an hour and filtered. To the filtrate was gradually added a cold solution of 3 g. anhydrous dimethylamine (0.065 mole) in 30 ml. dry tetrahydrofuran at 0° to 5° C. The mixture was stirred for 2 hours at 0° to 5° C., filtered and the solvent evaporated. The residue distilled under reduced pressure to give a fraction having b.p. 102° C./0.5 mm. which solidified on cooling. After crystallization from petroleum ether (60°–80° C.) the pure product, 1-dimethylcarbamoyl-4(5)-tert.butylimidazole, m.p. 85°–86° C., was isolated. The current state of our knowledge indicates that this compound is 1-dimethylcarbamoyl-4-tert.butylimidazole.

EXAMPLE 11

To a stirred solution of 62 g. 4-(1-methylcyclohexyl)imidazole in 85 ml. dry tetrahydrofuran and 56 ml. triethylamine was gradually added 45 g. dimethylcarbamoyl chloride. An exothermic reaction ensued and the rate of addition of dimethylcarbamoyl chloride was adjusted so as to maintain a gentle boiling of the reaction mixture under reflux. When addition of the dimethylcarbamoyl chloride was complete, the reaction mixture was boiled under reflux with stirring for one hour, and then cooled to room temperature. The reaction mixture was diluted with 200 ml. water and then extracted with ether (2 × 200 ml.). The ethereal extracts were combined, washed with water and dried over anhydrous sodium sulphate. After evaporation the resulting residue was crystallized from light petroleum (b.p. 60°–80° C.) to give the product, 1-dimethylcarbamoyl-4(5)-(1-methylcyclohexyl)imidazole, m.p. 72°–73° C. The current state of our knowledge indicates that this compound is 1-dimethylcarbamoyl-4-(1-methylcyclohexyl)imidazole.

The 4-(1-methylcyclohexyl)imidazole used in the above reaction was prepared in the following way.

A solution of 328 g. bromine in 300 ml. chloroform was added gradually to a stirred solution of 300 g. 1-methylcyclohexyl methyl ketone in 100 ml. methanol. After the addition of a few drops of bromine solution at 15° C. the reaction mixture was cooled and maintained between 0°–5° C. The reaction mixture was stirred for 10 minutes, after the addition of bromine had been completed, and then poured on to a mixture of crushed ice and water. The water layer was separated from the organic liquid and extracted with methylene chloride. The extract and the organic portion were combined and washed with water followed by a saturated solution of sodium bicarbonate and then finally with water. After drying over calcium chloride the liquid was evaporated and distilled to give bromomethyl 1-methylcyclohexyl ketone, b.p. 76°–78° C./0.1 mm Hg.

A mixture of 387 g. bromomethyl 1-methylcyclohexyl ketone and 1000 ml. formamide was heated with stirring. A stream of ammonia was passed through the reaction mixture over a period of one hour, the mixture being maintained at a temperature of 140°–160° C. After the passage of ammonia had been completed the reaction mixture was heated to 180°–190° C. The reaction mixture was maintained at this temperature for a period of two hours. Excess of formamide was evaporated under reduced pressure and the residue diluted with a little warm water and made alkaline with potassium carbonate. The resulting mixture was extracted with ether. After separation the ethereal extract was washed with water, dried over sodium sulphate, evaporated and distilled to give the novel intermediate 4-(1-methylcyclohexyl)imidazole, b.p. 146°–148° C./0.2 mm. Hg. The distillate crystallized from petroleum ether (b.p. 60°–80° C.) to give the product, m.p. 73°–75° C.

In an analogous manner to that described above, there were prepared the following compounds
1-dimethylcarbamoyl-4(5)-cyclohexylimidazole, m.p. 107°–108° C. (crystallized from petroleum ether, b.p. 100°–120° C.)
1-dimethylcarbamoyl-4(5)-(1-methylcyclopentyl)imidazole, m.p. 73° C. (crystallized from petroleum ether, b.p. 60°–80° C.)

The current state of our knowledge indicates that the 4(5) cycloalkyl groups of the imidazoles listed above are predominantly or substantially in the 4-position.

In the course of preparing the above imidazoles, the following novel intermediate was made.
4-(1-methylcyclopentyl)imidazole, m.p. 33°–35° C; b.p. 136°–140° C./0.5 mm.

EXAMPLE 12

To a stirred solution of 9.6 g. of 4-(1-methylcyclohexyl)imidazole and 14 ml. triethylamine in 80 ml. tetrahydrofuran was gradually added 11.9 g. morpholinocarbonyl chloride. An exothermic reaction ensued and the rate of addition of dimethylcarbamoyl chloride was adjusted so as to maintain a gentle boiling of the reaction mixture under reflux. When addition of the morpholinocarbonyl chloride was complete, the reaction mixture was boiled under reflux with stirring for 5 hours, and then cooled to room temperature. The reaction mixture was diluted with 200 ml. water and then extracted with ether (2 × 200 ml.). The ethereal extracts were combined, washed with water and dried over anhydrous sodium sulphate. After evaporation the resulting residue was crystallized from petroleum ether (b.p. 80°–100° C.) to give the product, 1-morpholinocarbonyl-4(5)-(1-methylcyclohexyl)imidazole, m.p. 127°–128° C.

The 4-(1-methylcyclohexyl)imidazole used in the above reaction was prepared as in Example 11.

In an analogous manner to that described above, there was prepared the following compound.

1-morpholinocarbonyl-4(5)-(1-methylcyclopentyl)imidazole, m.p. 82°–83° C. (crystallized from petroleum ether, b.p. 60°–80° C.)

The current state of our knowledge indicates that the 1-methylcycloalkyl groups of the above compounds are in the 4-position.

EXAMPLE 13

In an analogous way to that described in Example 11, there were prepared the following compounds.

1-piperidinocarbonyl-4(5)-(1-methylcyclohexyl)imidazole, m.p. 85°–87° C.
1-pyrrolidinylcarbonyl-4(5)-(1-methylcyclohexyl)imidazole, m.p. 110°–111° C.
1-pyrrolidinylcarbonyl-4(5)-(1-methylcyclopentyl) imidazole, m.p. 87°–89° C.
1-piperidinocarbonyl-4(5)-(1-methylcyclopentyl) imidazole, m.p. 77°–79° C.
1-dimethylcarbamoyl-4(5)-(1-methylcyclopentyl) imidazole, m.p. 64°–65° C.
1-(N-ethyl-N-methylcarbamoyl)-4(5)-(1-methylcyclopentyl) imidazole, 47°–49° C.

The current state of our knowledge indicates that the above compounds were obtained predominantly or substantially as the 4-substituted compounds.

EXAMPLE 14

A mixture of 20.1 g. 4-(1,3-dimethylcyclohexyl)imidazole, 150 ml. dry tetrahydrofuran, 28 ml. triethylamine and 16.2 g. dimethylcarbamoyl chloride were refluxed on a steam bath for an hour and then cooled. Methylene chloride was added and the solution washed with water, the first washing being re-extracted with methylene chloride. The methylene chloride extracts were dried over magnesium sulphate solution. After filtration the solution was evaporated to give the product, 1-dimethylcarbamoyl-4(5)-(1,3-dimethylcyclohexyl)imidazole, b.p. 138°–140° C/0.08 mm. The current state of our knowledge indicates that this product is predominantly 1-dimethylcarbamoyl-4-(1,3-dimethylcyclohexyl) imidazole.

The 4-(1,3-dimethylcyclohexyl) imidazole used in the above reaction was prepared in the following way.

A solution of 75 ml. (1.465 mole) bromine in 250 ml. chloroform was added dropwise to a stirred solution of 235 g. 1,3-dimethylcyclohexyl methyl ketone in 71 ml. methanol whilst maintaining the temperature of 0°–5° C. (the reaction was started by addition of a few drops of bromine solution at 15° C. then cooled to 0° C. and continued). The reaction mixture was stirred at 0°–5° C. for 10 minutes after the addition of bromine solution was complete, then poured on to crushed ice and water mixture. After extracting the water layer with methylene chloride, the methylene chloride was added to the organic portion and the mixture washed with water, saturated sodium bicarbonate solution and dried over calcium chloride. The solvent was evaporated and distillation gave the novel compound, bromomethyl-1,3-dimethylcyclohexyl ketone, b.p. 86°–89° C./0.1 mm.

A mixture of 265 g. bromomethyl-1,3-dimethylcyclohexyl ketone and 645 ml. formamide was heated with stirring. A weak stream of ammonia was passed through at 140° C. and the temperature raised from 140°–160° C. for one hour. The stream of ammonia was then stopped and the reaction mixture heated to 180°–190° C. for 2 hours. Excess formamide was evaporated under reduced pressure, the residue diluted with a little warm water and basified with potassium carbonate. The imidazole was separated with ether, washed with water and dried over sodium sulphate. After evaporation of the ether, the novel product was distilled over, 4-(1,3-dimethylcyclohexyl)imidazole, b.p. 140°–142° C./0.15 mm.

In an analogous manner to that described above, there were prepared the following compounds.

1-diethylcarbamoyl-4(5)-(1-ethylcyclohexyl)imidazole, b.p. 140° C./0.2 mm.
1-morpholinocarbonyl-4(5)-(1,3-dimethylcyclohexyl)imidazole, b.p. 160°–162° C./0.02 mm.
1-dimethylthiocarbamoyl-4(5)-(1-methylcyclohexyl)imidazole, b.p. 210°–214° C./3.0 mm.
1-diethylthiocarbamoyl-4(5)-(1-methylcyclohexyl)imidazole, b.p. 159°–164° C./0.3 mm.
1-dimethylcarbamoyl-4(5)-(1,3,3-trimethylcyclohexyl) imidazole, b.p. 142°–144° C./0.1 mm.
1-(N-methyl-N-2-butoxyethylcarbamoyl)-4(5)-(1-methylcyclohexyl)imidazole, b.p. 166°–175° C./0.6 mm.
1-morpholinocarbonyl-4-(1,3-dimethylcyclohexyl)imidazole, b.p. 160°–162° C./0.025 mm.
1-(N-methyl-N-2-ethoxyethylcarbamoyl)-4(5)-(1-methylcyclohexyl)imidazole, b.p. 210°–215° C./4.5 mm.

The current state of our knowledge indicates that the above compounds were obtained predominantly or substantially as the 4-substituted compounds.

EXAMPLE 15

To a solution of 12.8 g. 2-methyl-4(5)-(1-methylcyclopentyl)imidazole in a mixture of 60 ml. tetrahydrofuran and 20 ml. triethylamine was added 10.5 g. dimethylcarbamoyl chloride. The resulting mixture was boiled under reflux with stirring for 3½ hours, then cooled and diluted with 250 ml. methylene chloride. The solution thus formed was washed with water and then dried over anhydrous magnesium sulphate. After evaporating the solvent, the liquid residue distilled to give the product, 1-dimethylcarbamoyl-2-methyl-4(5)-(1-methylcyclopentyl)imidazole, b.p. 124°–6° C./0.1 mm. The current state of our knowledge indicates that this product was predominantly the 4-substituted derivative, 1-dimethylcarbamoyl-2-methyl-4-(1-methylcyclopentyl)imidazole.

The 2-methyl-4(5)-(1-methylcyclopentyl) imidazole used in the above reaction was prepared in the following way.

42 g. Bromomethyl 1-methylcyclopentyl ketone was added to a solution of 31.5 g potassium acetate in 300 ml. methanol and the resulting mixture was refluxed on a steam bath for two hours. It was then cooled, filtered and the filtrate added with stirring to a solution of 83 g. cupric acetate monohydrate in a mixture of 500 ml. water and 435 ml. 25 percent ammonia. A solution of 18.5 g. acetaldehyde in 100 ml. water was then added and the mixture heated on a steam bath for five hours with constant stirring.

After cooling the cuprous salt of the imidazole was collected, washed with water and suspended in 270 ml. of 4N acetic acid. While stirring, a solution of 34 g. potassium ferricyanide in 100 ml. water was added, and the precipitated copper complex removed and washed well with water. The combined supernatant liquors were basified to pH 9-10 with 5N sodium hydroxide and extracted several times with ether. The ethereal extracts were combined, washed with water and dried over anhydrous sodium sulphate. After evaporation of the solvent, the residue was crystallized from acetone to give the novel imidazole 2-methyl-4(5)-(1-methylcyclopentyl)imidazole, m.p. 108° C.

In an analogous manner to that described above, there were prepared the following compounds.

1-dimethylcarbamoyl-2-ethyl-4(5)-(1-methylcyclopentyl) imidazole, b.p. 118°-120° C./0.1 mm.
1-dimethylcarbamoyl-2-propyl-4(5)-(1-methylcyclopentyl) imidazole, b.p. 128°-130° C./0.15 mm.
1-dimethylcarbamoyl-2-methyl-4(5)-(1-methylcyclohexyl) imidazole, b.p. 135°-136°0 C/0.15 mm.
1-dimethylcarbamoyl-2-ethyl-4(5)-(1-methylcyclohexyl) imidazole, b.p. 134°-136° C./0.1 mm.
1-dimethylcarbamoyl-2-propyl-4(5)-(1-methylcyclohexyl) imidazole, b.p. 140°-142° C./0.1 mm.

The current state of our knowledge indicates that these imidazoles were obtained predominantly or substantially as the 4-substituted compounds.

In the course of preparing the above imidazoles, the following novel intermediates were made.

| | |
|---|---|
| 2-ethyl-4-(1-methylcyclopentyl)imidazole, 128°-131° C./0.1 mm., m.p. 87°-88° C. | b.p. |
| 2-propyl-4-(1-methylcyclopentyl)imidazole, 132°-136° C./0.15 mm. | b.p. |
| 2-methyl-4-(1-methylcyclohexyl)imidazole 112°-113° C. | m.p. |
| 2-ethyl-4-(1-methylcyclohexyl)imidazole 136°-138° C./0.15 mm. | b.p. |
| 2-propyl-4-(1-methylcyclohexyl)imidazole 140°-142° C./0.15 mm. | b.p. |

EXAMPLE 16

To a solution of 9.5 g. 2-ethyl-4-cyclopropylimidazole in 50 ml. dry tetrahydrofuran and 22 ml. triethylamine was added 8 g. dimethylcarbamoyl chloride. The resulting mixture was boiled under reflux for 3½ hours, then cooled and diluted with 250 ml. methylene chloride. After washing with water, the methylene chloride solution was dried over magnesium sulphate. Evaporation of the solvent gave a residue which distilled under reduced pressure to give the product, 1-dimethylcarbamoyl-2-ethyl-4(5)-cyclopropylimidazole, b.p. 118°-119° C./0.2 mm.

The current state of our knowledge indicates that this compound is 1-dimethylcarbamoyl-2-ethyl-4-cyclopropylimidazole.

The imidazole reactant was prepared in the following way.

110 g. Cyclopropane carbonylchloride dissolved in 150 ml. of absolute ether was added dropwise into an ice-cold solution of 91 g. diazomethane in 1500 ml. ether. After the addition was complete the temperature of the solution was allowed to rise to room temperature and to stand over night. The removal of the ether by distillation under reduced pressure left a yellow oil which was carefully mixed with 2000 ml. 2N sulphuric acid whilst cooling. This mixture was stirred at 50° C. for 5 hours and then cooled, neutralised with solid potassium carbonate and extracted with ether. The ethereal extract was evaporated the residue being distilled under reduced pressure to give cyclopropyl hydroxymethyl ketone, b.p. 56°-60° C./10 mm.

A solution of 40 g. cyclopropyl hydroxymethyl ketone in 350 ml. methanol was added with stirring to a solution of 160 g. cupric acetate monohydrate in 840 ml. water and 840 ml. 25 per cent ammonia, followed by the addition of 28 g. propionaldehyde. The resulting mixture was heated on a steam bath for five hours with constant stirring. Precipitation of the cuprous salt occured and, after cooling, the precipitate was collected, washed with water and suspended in 450 ml. 4N-acetic acid. While stirring, a solution of 66.5 g. potassium ferricyanide in 200 ml. water was added. The precipitated copper complex was removed and washed with water. The combined supernatant liquors were basified to pH 9 with 5N sodium hydroxide and extracted several times with ether. After combining the ethereal extracts, washing with water and drying over sodium sulphate, the solvent was evaporated. On standing the residue solidified and was crystallized from petroleum ether to give the novel 4-cyclopropyl-2-ethylimidazole, m.p. 104°-106° C.

EXAMPLE 17

An emulsifiable concentrate suitable for dilution with water to form an aqueous emulsion was prepared from the following ingredients:

| | % w/v |
|---|---|
| Compound of Example 1 | 20.0 |
| Calcium dodecylbenzenesulphonate | 2.0 |
| Nonylphenoxypolyethoxyethanol* | 4.0 |
| Cyclohexanone | 15.0 |
| Xylene | to 100.0 |

*A nonylphenol-ethylene oxide condensate containing an average of 14 mols. ethylene oxide per mol. nonylpheno.

Similar emulsifiable concentrates were prepared in which the imidazole compound in the above formulation was replaced by the following compounds of Example 3:

1-dimethylthiocarbamoyl-4(5)-tert.butylimidazole
1-(N-methyl-N-ethylcarbamoyl)-4(5)-tert-.butylimidazole
1-(N-methyl-N-propylcarbamoyl)-4(5)-tert-.butylimidazole
1-dimethylcarbamoyl-2-ethyl-4(5)-methylimidazole
1-dimethylcarbamoyl-4(5)-n-pentylimidazole

EXAMPLE 18

Emulsifiable concentrates suitable for dilution with water to form an aqueous emulsion were prepared from the following ingredients:

| | % w/v |
|---|---|
| Compound | 25.0 |

-continued

|  | % w/v |
|---|---|
| Calcium dodecylbenzenesulphonate* | 2.5 |
| Nonylphenoxypolyethoxyethanol | 2.5 |
| Xylene | to 100.0 % vol |

*A nonylphenol-ethylene oxide condensate containing an average of 14 mols. ethyleneoxide per mol. nonylphenol.

Emulsifiable concentrates containing the following compounds were prepared.
1-dimethylcarbamoyl-4(5)-isobutylimidazole
1-dimethylcarbamoyl-4(5)-(1-ethylpropyl)imidazole
1-dimethylcarbamoyl-4(5)-sec.butylimidazole
1-dimethylcarbamoyl-4(5)-isopropylimidazole
1-dimethylthiocarbamoyl-4(5)-sec.butylimidazole
1-dimethylcarbamoyl-4(5)-propylimidazole
1-dimethylcarbamoyl-4(5)-tert.pentylimidazole
1-(N-2-ethoxyethyl-N-methylcarbamoyl)-4(5)-tert.butylimidazole

EXAMPLE 19

Granules containing 5% w/w of the imidazole compound of Example 1 were prepared by impregnating granules of fullers earth (mesh size 20/40 British Standard Sieve) with a solution of the imidazole compound in xylene and then evaporating the xylene from the impregnated granules.

EXAMPLE 20

Granules containing 5% w/w of the 1-dimethylcarbamoyl-4(5)-(1-methylcyclohexyl)imidazole were prepared by impregnating granules of fullers earth (mesh size 20/40 British Standard Sieve) with a solution of the imidazole compound in xylene and then evaporating the xylene from the impregnated granules.

EXAMPLE 21

An emulsifiable concentrate suitable for dilution with water to form an aqueous emulsion was prepared from the following ingredients:

| 1-dimethylcarbamoyl-4(5)-(1-methylcyclohexyl)imidazole | 25.0% w/v |
|---|---|
| Calcium dodecylbenzenesulphonate | 2.5% w/v |
| Nonylphenoxypolyethoxyethanol* | 2.5% w/v |
| Cyclohexanone | 20.0% vol. |
| Xylene | to 100.0% vol. |

*A nonylphenol-ethylene oxide condensate containing an average of 14 mols. ethylene oxide per mol. nonylphenol.

Similar emulsifiable concentrates were prepared in which the imidazole compound in the above formulation was replaced by the remaining compounds of the invention described in Example 11.

EXAMPLE 22

A dispersible powder was prepared from the following ingredients:

|  | % w/w |
|---|---|
| 1-dimethylcarbamoyl-4(5)(1-methylcyclohexyl)imidazole | 25.0 |
| Nonylphenoxypolyethoxyethanol* | 1.0 |
| Dyapol PT* | 5.0 |
| Kaolin | to 100.0 |

*A nonylphenol-ethylene oxide condensate containing an average of 14 mols. ethylene oxide per mol. nonylphenol. Dyapol PT is an anionic dispersant based on the sodium salt of a sulphonated condensation product of urea/formaldehyde and cresol.

EXAMPLE 23

Broad bean plants 3–5 cm. high were infested with aphids (*Megoura viciae*) and then sprayed with an aqueous dispersion containing 250 parts per million w/v of the imidazole compound of Example 1. Each plant was kept under a lamp glass for 24 hours and then examined. It was found that a complete kill on the aphids had been obtained. The aphid populations of control plants that had been treated with an aqueous spray not containing any test compound were not affected.

EXAMPLE 24

Broad bean plants 3–5 cm. high were infested with aphids (*Megoura viciae*) and then sprayed with an aqueous dispersion containing 250 parts per million w/v of each of the carbamoyl imidazole compounds described in Example 11. Each plant was kept under a lamp glass for 24 hours and then examined. It was found that all of the compounds completely kill off the aphids. The aphid populations on control plants that had been treated with an aqueous spray not containing any test compound were not affected.

EXAMPLE 25

Broad bean plants 3–5 cm. high were infested with aphids (*Megoura viciae*) and then sprayed with an aqueous dispersion containing 250 parts per million w/v of each of the carbamoyl imidazole compounds described in Examples 2 to 8 and 12 to 16. Each plant was kept under a lamp glass for 24 hours and then examined. It was found that all of the compounds gave at least a 50 per cent control of the aphids. The aphid populations on control plants that had been treated with an aqueous spray not containing any test compound were not affected.

EXAMPLE 26

Hop leaves infested with the hop aphid, *Phorodon humuli*, were treated with aqueous dispersions of various compounds.

Ten leaves were taken from each of four replicate plants and the average number of aphids per leaf calculated. The hop plants were sprayed with an aqueous dispersion of the test compound till run off. Assessment one day after spraying showed that with an aqueous dispersion containing 0.03 per cent by weight of the test compound, the following compounds achieved over 50 per cent kill.
1-dimethylcarbamoyl-4(5)-tert.butylimidazole
1-dimethylcarbamoyl-4(5)-isopropylimidazole
1-dimethylcarbamoyl-4(5)-(1-ethylpropyl)imidazole
1-dimethylcarbamoyl-4(5)-sec.butylimidazole
1-dimethylthiocarbamoyl-4(5)-sec.butylimidazole
1-dimethylcarbamoyl-4(5)-propylimidazole
1-dimethylcarbamoyl-4(5)-(1-methylcyclohexyl)imidazole
1-dimethylcarbamoyl-4(5)-tert.pentylimidazole

EXAMPLE 27

An assessement of ovo-larvicidal activity against *Tetranychus urticae* was made in the following way.

Freshly laid eggs of *Tetranychus urticae* on a French bean leaf disc 2 cm. in diameter were sprayed with an aqueous dispersion of the compound test. After ten days any live larvae on the leaf disc were counted and the percentage mortality assessed. Triplicate assessments were made at various concentrations of test compound in order to obtain approximately $LD_{50}$ values, expressed as p.p.m. w/v of test compound.

The following two compounds were found to have an $LD_{50}$ below 250 p.p.m.

1-dimethylcarbamoyl-4(5)-(1-methylcyclopentyl-)imidazole 1-dimethylcarbamoyl-4(5)-(1-methylcyclohexyl-)imidazole

EXAMPLE 28

An assessment of the activity of 1-dimethylcarbamoyl-4(5)-tert.butylimidazole against the green rice leafhopper was made in the following way.

The roots of a rice seedling were dipped in an aqueous emulsion containing 0.005% by weight of the test compound. The rice seedling was enclosed in a glass cylinder into which fifteen adult green rice leafhoppers were inserted and the temperature was maintained at 25° C.

After 48 hours the insect mortality was observed. It was found that a complete kill of the insects had occurred.

We claim:

1. A compound of the formula

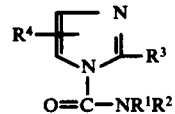

in which $R^3$ is selected from the group consisting of hydrogen, methyl and ethyl, $R^4$ is an alkyl group selected from the group consisting of tert.butyl, sec.butyl, propyl, 1-ethylpropyl, isopropyl and tert.pentyl, and $R^1$ and $R^2$ are both methyl.

2. A compound according to claim 1 in which $R^3$ is hydrogen.

3. 1-dimethylcarbamoyl-4(5)-tert.butylimidazole.

4. 1-dimethylcarbamoyl-4(5)-sec.butylimidazole.